United States Patent [19]
Yarkony

[11] Patent Number: 5,143,087
[45] Date of Patent: Sep. 1, 1992

[54] ANALYSIS AND TREATMENT OF SWALLOWING DYSFUNCTION

[76] Inventor: Shirit Yarkony, 30 Agnon Street, Ramat-Aviv, Tel-Aviv, Israel

[21] Appl. No.: 660,678

[22] Filed: Feb. 25, 1991

[30] Foreign Application Priority Data

Mar. 1, 1990 [IL] Israel .................................. 93587

[51] Int. Cl.$^5$ .............................................. A61B 5/103
[52] U.S. Cl. ...................................................... 128/780
[58] Field of Search ........................ 128/774, 777, 780

[56] References Cited

U.S. PATENT DOCUMENTS

| | | | |
|---|---|---|---|
| 3,480,003 | 11/1969 | Crites .................... | 128/780 |
| 3,939,823 | 2/1976 | Kaye et al. ............. | 128/780 |
| 4,214,593 | 7/1980 | Imbruce et al. ........ | 128/780 |
| 4,359,726 | 11/1982 | Lewiner et al. ........ | 340/666 |
| 4,561,450 | 12/1985 | Bryant .................. | 128/780 |
| 4,757,194 | 7/1988 | Simms ................... | 128/780 |

FOREIGN PATENT DOCUMENTS

| | | | |
|---|---|---|---|
| 0074114-A1 | 3/1983 | European Pat. Off. | |
| 0014693-B1 | 6/1983 | European Pat. Off. | |
| 0762854 | 9/1980 | U.S.S.R. ................ | 128/780 |
| 2138144-A | 10/1984 | United Kingdom. | |

OTHER PUBLICATIONS

Shawker et al., "Ultrasound Analysis of Tongue, Hyoid, and Larynx Activity During Swallowing", *Investigative Radiology*, Mar.-Apr. 1984 at 82–86.

Cranen et al., "Pressure measurements during speech production using semiconductor miniature pressure transducers: Impact on models for speech production", *J. Acoust. Soc. Am.*, 77 (Apr. 1985) at 1543–1551.

Fraden, "Application of Piezo/Pyroelectric Films in Medical Transducers", *J. Clinical Engineering*, 13, (Mar.-Apr. 1988) at 133–138.

Reddy et al., "Biomechanical Quantification for Assessment and Diagnosis of Dysphagia", *IEEE Engineering Med. Bio.*, (Sep. 1988) at 16–20.

Sonies et al., "Evaluation of Swallowing Pathophysiology", *Otolaryngologic Clinics N. Am.* (Nov. 1988) at 637–648.

Lee et al., "Quantitative Analysis of Dysphagia: Development of a Tongue Force Measurement System", *Proceedings of Annual International Conf. of IEEE Engineering Med. Bio. Soc.*, (Nov. 9, 1989) at 1624–1625.

*Primary Examiner*—Max Hindenburg
*Attorney, Agent, or Firm*—Merchant & Gould Smith, Edell, Welter & Schmidt

[57] ABSTRACT

A method of analyzing the swallowing of a subject, comprises providing displacement and/or presssure-activated transducing means which are positioned in the desired positioned relationship with the anatomical structure of the subject, the behavior of which during swallowing it is desired to analyze, e.g., the larynx of the subject. The signals generated by the transducing means when swallowing is performed are analyzed and elaborated to determine swallow beginning and ending time and the relative induced intensity of the sampled signals at the sampling times, and visual data or data points are provided, representing the induced intensity of the sampled signals representing the swallowing behavior of the subject.

Apparatus for carrying out the analysis and bio-feedback apparatus which utilize the method are also provided.

16 Claims, 3 Drawing Sheets

ANALYSIS AND TREATMENT OF SWALLOWING DYSFUNCTION

FIELD OF THE INVENTION

The present invention relates to the analysis and treatment of swallowing dysfunction.

BACKGROUND OF THE INVENTION

Swallowing dysfunction may occur in a human subject as a result of different physiological causes, and the analysis of the swallowing behavior of a subject may be useful in the diagnosis of a variety of illnesses. Furthermore, when abnormal swallowing behavior is found in a subject, it is important to recognize the problem and to educate the subject to properly perform the swallowing action.

THE PRIO ART

An analysis of this type of problem has been carried out in the art. For instance, Shawker et al. ["Ultra Sound Analysis of Tongue, Hyoid and Larynx Activity During Swallowing", Investigative Radiology, 1984, 9: 82-86] used a very complicated technique based on a combination of balloon pressure techniques and ultrasonic scanner techniques, to evaluate the behavior of a subject during swallowing. These authors followed the movement of the tongue with an ultrasonic scanner, and the activity of the larynx with an external device. The results they obtained with respect to the movement of the larynx were difficulty repeatable, as in two out of ten subjects the first out of two swallows was used for measurements because of difficulties with the laryngeal pressure transducer display, while in eight out of ten subjects analyzed only two swallows were followed, and the second swallow was arbitrarily chosen for analysis. The reason for this procedure is that the heavy equipment employed does not afford repetition of the results and cannot be kept on a subject for a long period of time. As will be understood by a person skilled in the art, this is a very severe drawback, as long time measurement and analysis of the behavior of a human subject are often necessary in order to be able to draw meaningful conclusions. Furthermore, ultrasonic techniques can be employed to follow the first oral stage of the swallowing activity, but are not useful to follow the frequency, speed or depth of the swallow.

In a recent review [Evaluation of Swallowing Pathophysiology, Otolaryngologic Clinics of North America, vol. 21, no. Nov., 4, 1988, pp. 637-647] Sonies and Baum reviewed the techniques available for the clinical evaluation of swallowing. The techniques detailed include the computerized axila tomography (CAT), ultrasound (US), x-rays (still and video fluoroscopy), magnetic resonance imaging (MRI), manometry and scintigraphy. All of these techniques are complicated, some of them require expensive and sophisticated apparatus, such as CAT, US, x-ray and MRI, some are invasive techniques such as manometry, and some require injection of foreign substances. It is therefore clear that it would be highly desirable to be able to provide a simple method for effectively analyzing the behavior of a subject during swallowing activity, which method could be carried out using simple and non-expensive apparatus that exploits non-invasive techniques, thus rendering it possible to perform extensive analysis of a large number of patients.

SUMMARY OF THE INVENTION

It is an object of the present invention to provide such a method, which overcomes the drawbacks of available methods and which can be used by the specialized physician in his clinics, thus making it possible to analyze a large number of patients.

It is another object of the invention to provide an apparatus for carrying out of the method, which is relatively non-expensive and which is simple in operation.

It is still another object of the invention to provide a method and apparatus which permit to carry out repetitive analyses of prolonged duration of swallowing activity, on the one hand, and detailed analysis of a single swallow and its stages on the other hand.

It is a further object of the invention to provide a method by means of which swallowing activity can be followed, and bio-feedback may be given to the patient, thus enabling the patient to correct his swallowing performance. Correctable swallowing parameters include-but are not limited to-the frequency of deglutition, the amplitude of a single swallow, the coordination and continuity in laryngeal movement, and the movement of additional anatomical structures involved in swallowing, such as the tongue, hyoid and oral muscles.

It is still another object of the invention to provide a bio-feedback apparatus which can be used by a physician or by the subject himself, which is simple in operation and effective.

It is an additional object of the invention to provide a bio-feedback apparatus which can be used by the person in need of treatment at his own home, after having been treated and/or analyzed by a competent physician, for the purpose of exercising the correct swallowing performance.

The method of analyzing the swallowing of a subject, according to the invention, comprises the steps of:

1) providing displacement and/or pressure-activated transducing means;

2) positioning the said transducing means in the desired positioned relationship with the anatomical structure of the subject, the behavior of which during swallowing it is desired to analyze, e.g., the larynx of the subject;

3) sampling the signals generated by the transducing means when swallowing is performed;

4) analyzing the signals to determine swallow beginning and ending time and the relative induced intensity of the sampled signals at the sampling times, which induced intensity depends on the movement of the anatomic structure that acts on the transducer; and 5) providing visual data or data points representing the induced intensity of the sampled signals representing the swallowing behavior of the subject.

Different signals can be provided for different swallow parameters. The swallow parameters will include, e.g., swallow beginning and ending time, the form, sequency, continuity and coordination of the various anatomical structures involved in swallowing, e.g., the larynx, tongue, hyoid and oral muscles.

As displacement and/or pressure-activated transducing means a variety of known devices can be employed. For instance, but without the intention of limiting the invention thereto, strain gauges can be employed, or piezo-electric transducers. Piezo-electric transducers are preferred, because they respond to light pressures, are lightweight and can be easily positioned near the larynx or other anatomical structure of the subject, but any comparable transducer that can be conveniently positioned on the subject can be likewise employed, as will be apparent to the skilled person. Futher, convenient piezo-electric material transducers are, e.g., piezo-electric films such as those manufactured by Pennwalt Corporation under the trade name Kynar. When piezo-electric films such as the Kynar film are used, it is also possible to provide matrix output in which different locations on the film independently produce a signal indicative of intensity and position when they are pressure-activated. In this way, it is possible to follow the movement of the larynx with time.

Examples of the transducers and of various conventional uses of such tranducers can be found, e.g., in European Patent Application No. 14,693, British Patent Application No. 2,138,144 and U.S. Pat. No. 4,359,726. The article by Fraden, J. "Application of Piezo/Pyroelectric Films In Medical Transducers", J. Clin. Engg., Mar./Apr. 1988, pp. 133-138, is also noteworthy.

Additionally, optical displacement transducers can be employed to generate signals relative to the swallowing activity, such as optical devices comprising optical fibers.

When the transducer is a contact-activated device, than it should be positioned accordingly, in contact with the structure to be monitored. When the transducer comprise optically activated elements, however, it may be possible to position it at a distance from the structure examined, depending on the actual nature of the sensor. The appropriate positioning of the transducer, of course, is within the skill of the routineer, and is dependent on the various types of transducers that are available or will be developed for future use.

It should be understood that throughout this specification, unless otherwise indicated, whenever reference is made to the monitoring of the movement of the larynx, it is meant to include all anatomic structures which are involved in swallowing, such as the tongue, hyoid and the oral muscles. Thus, for instance, when it is desired to analyze the movement of the tongue during swallowing, a transducer, e.g., a Kynar film, may be positioned on the tongue and removed or replaced at the end of each swallow.

Thus in accordance with the present invention, there is also provided an apparatus for analyzing the swallowing of a subject, which apparatus comprises:

1) displacement and/or pressure-activated transducing means;

2) means (e.g., an appropriate strap) for positioning the said transducing means in the desired positioned relationship with the anatomical structure of the subject, the behavior of which during swallowing it is desired to analyze, e.g., by securing them in close juxtaposition with the larynx of the subject;

3) sampling means for continuously or periodically sampling the signals generated by the transducing means. These may include, e.g., amplifying means which receive the electrical signals generated by the transducer, such as a piezo film, and amplifies them and/or translates them into signals that can be fed into a microprocessor;

4) analyzing means to analyze the said signals to determine swallow beginning and ending time and the relative induced intensity of the sampled signals at the sampling times, which analyzing means may include, e.g., an Analog-to-Digital transducer; and 5) visual data or data points display means to display the data points representing the induced intensity of the sampled signals.

The analyzing means may comprise a microprocessor or a microcomputer. Preferably, a personal computer, such as an IBM PC, is employed for this purpose. Then, the signals generated by the transducing means and transmitted and received by the sampling means would be fed into the microcomputer by means known to the skilled person and which need not be discussed here.

The display means may be any type of display which enables the physician to view the results of the analysis. Often a display such as the normal display of a personal computer will be used for first review, but it may be desirable, for more detailed analysis and for record keeping, to provide a printed record of the results of the analysis. For this purpose the display means will often comprise a printer or a plotter. Furthermore, the data created during the analyses can be stored, for future reference and analysis, on any appropriate storage means, e.g., a magnetic or an optical disk, or the hard disk of a PC.

The invention further embraces a method of signaling to a subject who does not correctly perform his swallowing activity, so that the subject may educate himself to perform an improved swallow, by means of biofeedback swallowing techniques, which method comprises the steps of:

1) providing displacement and/or pressure-activated transducing means;

2) positioning the said transducing means in the desired positioned relationship with the anatomical structure of the subject, the behavior of which during swallowing it is desired to analyze, e.g., the larynx of the subject;

3) sampling the signals generated by the transducing means when swallowing is performed;

4) analyzing the signals to determine the interval of time between two separate swallows and the relative induced intensity of the sampled signals at the sampling times;

5) determining whether the interval between two separate swallows exceeds a predetermined interval of time, and if the predetermined interval of time is exceeded, generating a signal to prime the subject to perform a swallow; and 6) for each swallow parameter analyzed, determining whether the intensity and/or the sequency of the sampled signals departs from a predetermined value or range of values, and if the value and/or the sequency of the sampled signal departs from the said predetermined value or range of values, generating a signal to prime the subject to perform a correct swallow. Thus, for instance, in a subject who does not perform deep enough swallows, the value of the sampled signal will indicate the depth of the swallow, and the predetermined value of the signal will be the minimal acceptable depth of swallow. Thus, if the subject does not swallow deeply enough, the value of the sampled signal will be below the minimal predetermined depth of swallow and a signal will be generated to prime the subject to perform a deeper swallow. If, on the other hand, the sequence of the stages is incorrect, an appropriate signal will be generated, which may be different in type and/or intensity from signals generated, e.g., by a non-deep-enough swallow.

DETAILED DESCRIPTION OF THE INVENTION

Detailed Description of Preferred Embodiments

Figure 1:
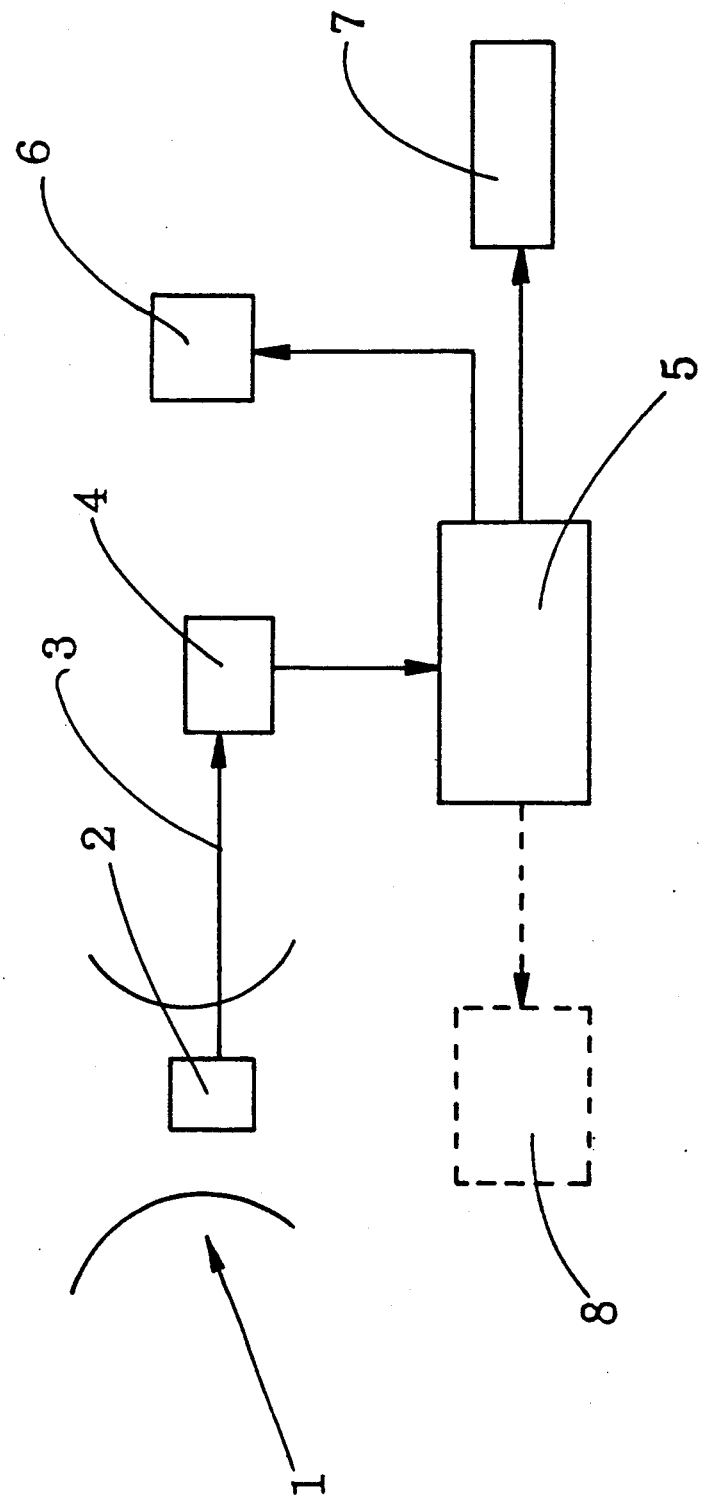
FIG. 1 is a schematic representation of the set-up of an apparatus according to one embodiment of the invention.

To further illustrate the invention, reference is now made to FIG. 1 which schematically shows a representative set-up of an apparatus according to one embodiment of the invention, which can be used to carry out the method of the invention. The zone of the subject which is to be analyzed, e.g., the neck (larynx) or tongue, is schematically indicated by numeral 1, and the transducer, e.g., a piezo-electric transducer, is indicated by numeral 2. The electric signals generated by piezo transducer 2 are transmitted, through wire 3, to sampling means 4, whic hmay be, e.g., an amplifier, which may be further coupled to an A-to-D card. Normally, the A-to-D card will be contained within the computer, and if no amplifier is required it may be directly connected to the output of the transducer 2.

A microprocessor, 5, receives the data from the sampling means 4 which, as said, may be integral with the microprocessor 5, and analyzes them. The data so analyzed, in form of data representing intensity versus time, can be displayed on a display 6, which may be the display of a personal computer, if microprocessor 5 is enclosed in a personal computer, and the same data may be additionally, or alternatively, printed out on a printer 7.

If it is desired to employ the apparatus of FIG. 1 as an apparatus for effecting the bio-feedback education of a patient, display means 6 and 7 can be dispensed with, and signaling means 8, indicated in broken lines in the figure, can be provided, which will signal to the patient that the performance of the swallow is below a desired performance. The signaling means 8 may be, for instance, acoustic signaling means, such as a beeper, or visual signaling means, such as a display or touch signaling means such as vibration/touch stimuli place in contact with the skin of the subject. Furthermore, two different types of signals as well as different intensities of the signal, may be provided, to indicate to the subject whether his swallow is deficient in frequency, depth, form, sequency, continuity or coordination, and to what extent. Of course, different signals can also be provided to indicate different deficiencies in swallowing. For instance, for the larynx and the hyoid the movement in two planes (AP/vertical), as well as the continuity of movement are important; the timing and sequency of events in swallowing will be considered with respect to all anatomical structures; the muscles the tensile contraction of the oral muscles can also be analyzed, etc.

The apparatus shown in FIG. 1 is an analysis apparatus which, as explained, can be used also as a bio-feedback apparatus. The invention, however, contemplates also providing simpler and cheaper devices that can be used by the patient to exercise, according to parameters preset by the physician as the result of the analyses effected. Thus, the simplified apparatus will still, broadly speaking, comprise the elements described with reference to FIG. 1, but will only be able to provide bio-feedback by way of signalling means. While, as explained, the analyzing apparatus of FIG. 1 can be employed "as is" as a bio-feedback device, this will normally be needlessly expensive and complicated for home exercise purposes.

Figure 2:
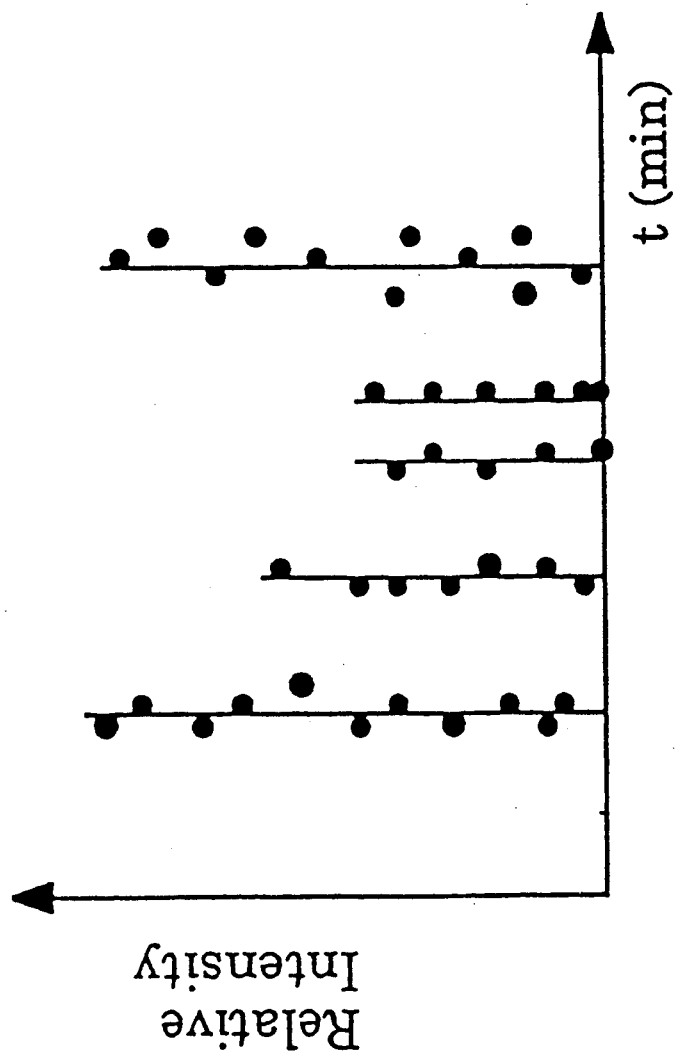
FIG. 2 schematically shows a number of swallows as displayed on a printer or on a display.

FIG. 2 schematically shows a number of swallows as can be displayed, e.g., on a printer or on the display of a PC. This figure shows the intensity of each swallow and all swallows occurring in the period of time examined. From the data points shown in the figure deficient swallowing, whether from the point of view of depth of swallowing or of frequency (time passing between two swallows) can be determined.

Figure 3:
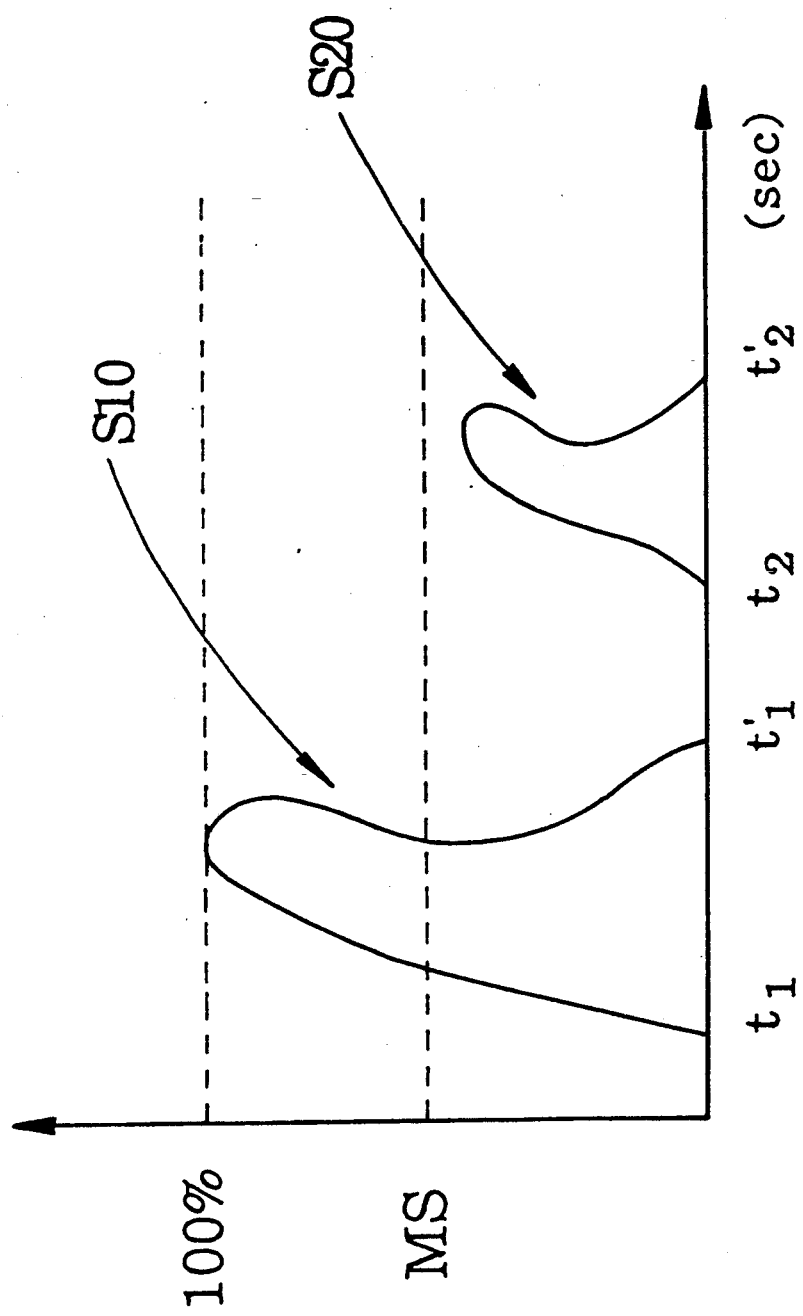
FIG. 3 illustrates the analysis of single swallows.

FIG. 3 shows the analysis of single swallows, two swallows being shown. The first swallow, indicated by S10, begins at time $t_1$ and ends at time $t'_1$. The maximum swallow is above the minimal intensity, MS, of the swallow which has been set for the specific subject. Thus, swallow S10 is a correct swallow, and will result in no signal from the system, if a bio-feedback system is employed. The second swallow, S20, begins at time $t_2$ and ends at time $t'_2$. This swallow has a maximum which is below the minimal relative intensity which is desirable for the subject. Thus, if a bio-feedback system is employed, a signal indicating to the subject that the depth of swallow is insufficient will be generated.

Furthermore, the time intervening between $t'_1$ and $t_2$ will be compared with a preset time interval. If the time interval $t_2-t'_1$ is shorter than the maximal preset time interval, then swallow S20 will occur spontaneously. On the other hand, if the time interval reaches the value of the maximal permissible time interval, then a signal will be generated to prime the subject to effect the next swallow at the time $t_2$, and swallow S20 will be the result of this priming produced by the biofeedback apparatus. Additional information on the behavior of each swallow can be similarly obtained from the data for a single swallow.

All the above description and examples have been given for the purpose of illustration. Many different modifications can be made in the various devices, components and methods, without exceeding the scope of the invention.

I claim:

1. A method of analyzing the swallowing of a subject, comprising the steps of:
   1) providing displacement and/or pressure-activated transducing means;
   2) positioning the said transducing means in the desired positioned relationship with the anatomical structure of the subject, the behavior of which during swallowing it is desired to analyze, e.g., the larynx of the subject;
   3) sampling the signals generated by the transducing means when swallowing is performed;
   4) analyzing the signals to determine swallow beginning and ending time and the relative induced intensity of the sampled signals at the sampling times; and
   5) providing visual data or data points representing the induced intensity of the sampled signals representing the swallowing behavior of the subject.

2. A method according to claim 1, wherein the anatomic structure is selected from the larynx, hyoid, tongue and the oral muscles.

3. A method according to claim 1, wherein the pressure-activated transducing means comprise a strain gauge.

4. A method according to claim 1, wherein the pressure-activated transducing means comprise a piezo-electric transducer.

5. A method according to claim 4, wherein the piezo-electric transducer is a piezo film.

6. A method according to claim 5, wherein the piezo film is a Kynar film.

7. A method according to claim 5, wherein the piezo film is a matrix design piezo film sensor, which provides a plurality of pressure-induced signals at a plurality of positions therein.

8. Apparatus for analyzing the swallowing of a subject, which apparatus comprises:
 1) displacement and/or pressure-activated transducing means;
 2) means for positioning said transducing means in the desired positioned relationship with the anatomical structure of the subject, the behavior of which during swallowing it is desired to analyze, e.g., the larynx of the subject;
 3) sampling means for continuously or periodically sampling the signals generated by the transducing means;
 4) analyzing means to analyze the signals to determine swallow beginning and ending time and the relative induced intensity of the sampled signals at the sampling times; and
 5) visual data or data points display means to display the data representing the pressure-induced intensity of the sampled signals.

9. Apparatus according to claim 8, wherein the analyzing means comprise a microprocessor or a microcomputer, preferably a Personal Computer.

10. Apparatus according to claim 8, wherein the display means comprise a printer or a plotter.

11. Apparatus according to claim 8, wherein the displacement transducing means comprise optical sensing means.

12. Apparatus according to claim 11, wherein the optical sensing means comprise one or more optical fibers.

13. A method of signaling to a subject to perform an improved swallow, comprising the steps of:
 1) providing displacement and/or pressure-activated tranducing means;
 2) positioning the said transducing means in the desired positioned relationship with the anatomical structure of the subject, the behavior of which during swallowing it is desired to analyze;
 3) sampling the signals generated by the transducing means when swallowing is performed;
 4) analyzing the said signals to determine the interval of time between two separate swallows and the relative induced intensity of the sampled signals at the sampling times;
 5) determining whether the interval between two separate swallows exceeds a predetermined interval of time, and if the predetermined interval of time is exceeded, generating a signal to prime the subject to perform a swallow; and
 6) for each swallow parameter analyzed, determining whether the intensity and/or the sequency of the sampled signal departs from a predetermined value or range of values, and if the value and/or the sequency of the sampled signal departs from the said predetermined value or range of values, generating a signal to prime the subject to perform a correct swallow.

14. A biofeedback apparatus for signaling to a subject to perform an improved swallow, particularly for home use, comprising:
 1) displacement and/or pressure-activated transducing means;
 2) means for positioning the transducing means in the desired positioned relationship with the larynx or other anatomical structure of the subject;
 3) sampling means for continously or periodically sampling the signals generated by the transducing means;
 4) analyzing means to analyze the signals to determine swallow beginning and ending time and/or events sequency and the relative induced intensity of the sampled signals at the sampled times;
 5) comparing means to compare the relative induced intensities and/or sequencies to present limiting values; and
 6) signaling means for signaling the subject when the intensity and/or sequency of the sampled signals departs from the preset limiting value.

15. Apparatus according to claim 14, wherein the signal-producing means generates a beep tone and/or a visual signal and/or a touch signal.

16. A method of teaching a subject to perform an improved swallow, comprising the steps of:
 1) Analyzing the swallow performance of the subject by:
  (a) providing displacement and/or pressure activated transducing means;
  (b) positioning the said transducing means in the desired positioned relationship with the anatomical structure of the subject, the behavior of which during swallowing it is desired to analyze, e.g. the larynx of the subject;
  (c) sampling the signals generated by the transducing means when swallowing is performed;
  (d) analyzing the signals to determine swallow beginning and ending time and the relative induced intensity of the signals at the sampling times; and
  (e) providing visual data or data points representing the induced intensity of the sampled signals representing the swallowing behavior of the subject
 to determine the desired swallow parameter values and/or ranges for the specific subject;
 2) Presetting the desired swallow parameter values and/or ranges determined thereby in a bio-feedback apparatus; and
 3) Providing the subject with the bio-feedback apparatus and instructions.

* * * * *